(12) United States Patent
Xu

(10) Patent No.: US 8,823,954 B2
(45) Date of Patent: Sep. 2, 2014

(54) LOW COHERENCE ENHANCED BACKSCATTERING TOMOGRAPHY AND TECHNIQUES

(75) Inventor: Min Xu, Sunnyside, NY (US)

(73) Assignee: Fairfield University, Fairfield, CT (US)

( * ) Notice: Subject to any disclaimer, the term of this patent is extended or adjusted under 35 U.S.C. 154(b) by 123 days.

(21) Appl. No.: 13/698,360

(22) PCT Filed: May 17, 2011

(86) PCT No.: PCT/US2011/036744
§ 371 (c)(1),
(2), (4) Date: Nov. 16, 2012

(87) PCT Pub. No.: WO2011/149708
PCT Pub. Date: Dec. 1, 2011

(65) Prior Publication Data
US 2013/0063727 A1    Mar. 14, 2013

Related U.S. Application Data

(60) Provisional application No. 61/347,663, filed on May 24, 2010.

(51) Int. Cl.
*G01B 11/14* (2006.01)
*G01B 9/02* (2006.01)
*G01B 11/24* (2006.01)
*A61B 5/00* (2006.01)
*G01N 21/47* (2006.01)

(52) U.S. Cl.
CPC ............. *G01N 21/4795* (2013.01); *G01B 9/02* (2013.01); *G01B 11/24* (2013.01); *G01B 11/14* (2013.01); *A61B 5/0066* (2013.01)

USPC ........... 356/625; 356/446; 356/128; 356/303; 382/131; 600/104; 435/29; 435/288.7

(58) Field of Classification Search
CPC ..... G01B 9/02; G01N 21/4795; A61B 5/0066
USPC ................. 356/625, 446, 128, 303; 382/131; 600/104; 435/29, 288.7
See application file for complete search history.

(56) References Cited

U.S. PATENT DOCUMENTS

| | | | |
|---|---|---|---|
| 7,061,622 B2 * | 6/2006 | Rollins et al. | 356/497 |
| 7,652,772 B2 * | 1/2010 | Backman et al. | 356/497 |
| 7,667,832 B2 * | 2/2010 | Backman et al. | 356/128 |

(Continued)

OTHER PUBLICATIONS

Xu et al., Journal of Biomedical Optics, 13(2) Mar./Apr. 2008.

*Primary Examiner* — Tarifur Chowdhury
*Assistant Examiner* — Isiaka Akanbi
(74) *Attorney, Agent, or Firm* — Cantor Colburn LLP

(57) ABSTRACT

A low coherence enhanced backscattering tomography (LEBT) method is disclosed for depth-selective sensing of the superficial layer of tissue. 3D images of the microarchitecture and molecular conformation of the superficial layer of tissue are obtained. The method combines the high resolution advantage of low coherence light and the high sensitivity advantage of light scattering to tissue structure and composition. Intact tissue can be examined without the need of excision or processing. The method can be applied in in situ measurements. According to the method, 3D images of the nuclear morphology and cellular structure for the superficial layer of the tissue are generated; this is particularly useful in detecting cancer and precancer at the earliest stage of carcinogenesis.

20 Claims, 14 Drawing Sheets

$$\mu_s p(\theta) = \mu_{s,Mie} p_{Mie}(\theta) + \mu_{s,bg} p_{bg}(\theta) = \begin{cases} \mu_{s,Mie} p_{Mie}(\theta) & \text{small angle scattering} \\ \mu_{s,bg} p_{bg}(\theta) & \text{large angle scattering} \end{cases}$$

(56) References Cited

U.S. PATENT DOCUMENTS

| | | |
|---|---|---|
| 7,982,879 B2 * | 7/2011 | Desjardins et al. ........... 356/477 |
| 2007/0201033 A1 * | 8/2007 | Desjardins et al. ........... 356/497 |
| 2008/0037024 A1 | 2/2008 | Backman et al. |
| 2008/0278713 A1 * | 11/2008 | Backman et al. ............. 356/128 |
| 2009/0009759 A1 | 1/2009 | Backman et al. |
| 2009/0317856 A1 | 12/2009 | Mycek et al. |

* cited by examiner $$\mu_S p(\theta) = \mu_{S,\text{Mie}} p_{\text{Mie}}(\theta) + \mu_{S,\text{bg}} p_{\text{bg}}(\theta) = \begin{cases} \mu_{S,\text{Mie}} p_{\text{Mie}}(\theta) & \text{small angle scattering} \\ \mu_{S,\text{bg}} p_{\text{bg}}(\theta) & \text{large angle scattering} \end{cases}$$

FIG. 1-1

$$I_{\text{CBS}}(q_\perp) = 2\pi \int_0^{+\infty} \rho d\rho I(\rho) J_0(q_\perp \rho) \left[ 2\frac{J_1(\rho/L_c)}{\rho/L_c} \right]^2$$

FIG. 1-2

$$\frac{1}{I_{\text{CBS}}^{(2)}(\lambda, \theta=0)} \propto 2 + \frac{\mu_{S,\text{bg}}(\lambda)}{\mu_{S,\text{Mie}}(\lambda)} + \frac{\mu_{S,\text{Mie}}(\lambda)}{\mu_{S,\text{bg}}(\lambda)}$$

FIG. 1-3

$$I(\rho) = \frac{1}{(2\pi)^2} \mu_{S,\text{bg}} p_{\text{bg}}(\pi) \int_0^{+\infty} dz \exp(-2\mu_T z)$$
$$\times \int d\kappa \exp(i\kappa \cdot \rho) \left\{ \exp\left[ 2\mu_{S,\text{Mie}} \int_0^z \chi_{\text{Mie}}(\kappa\xi) d\xi \right] - 1 \right\}$$

FIG. 1-4

$$I_{CBS}(q_\perp) = \int_0^{+\infty} dz I_{CBS}(q_\perp, z)$$

FIG. 1-5

$$I_{CBS}(q_\perp, z) = \frac{L_c^2}{(2\pi)^2} \mu_{s,bg} P_{bg}(\pi) \exp(-2\mu_T z) \int dp \left[ 4 \arccos\left(\frac{pL_c}{2}\right) - pL_c \sqrt{4 - p^2 L_c^2} \right]$$
$$H(2 - pL_c) \left\{ \exp\left[ 2\mu_{s,Mie} \int_0^z \chi_{Mie}(|p - q_\perp|\xi) d\xi \right] - 1 \right\}$$

FIG. 1-6

$$z_{max} = \frac{\int_0^{+\infty} dz I_{CBS}(q_\perp, z) z}{\int_0^{+\infty} dz I_{CBS}(q_\perp, z)}$$

FIG. 1-7

$$f(a,b,N_{Mie},c) = \frac{1}{2}\sum_{i=1}^{N\lambda}\sum_{j=1}^{N\theta}[I_{CBS}(\lambda_i,\kappa\theta_j;L_c) - \mathcal{I}(\lambda_i,\theta_j;L_c)]^2$$

FIG. 1-8

$$I_{CBS}(\lambda,q_\perp) = \sum_{l=1}^{Nz} I_{CBS,l}(\lambda,q_\perp)\Delta z$$

FIG. 1-9

$$I_{CBS}(\lambda,q_\perp) = \frac{L_c^2}{(2\pi)^2}\mu_{S,bg}^{(l)}p_{bg}^{(l)}(\pi)\exp\left[-2\sum_{i=1}^{l}\mu_T^{(i)}\Delta z\right]\int dp \left[4\arccos\left(\frac{pL_c}{2}\right) - pL_c\sqrt{4-p^2L_c^2}\right]$$
$$H(2-pL_c)\left\{\exp\left[2\sum_{i=1}^{l}\mu_{S,Mie}^{(i)}\int_{(i-1)\Delta z}^{i\Delta z}\chi_{Mie}^{(i)}(|p-q_\perp|\xi)d\xi\right]-1\right\}$$

FIG. 1-10

$$F(x) = \frac{1}{2} \sum_{i=1}^{N\lambda} \sum_{j=1}^{N\theta} \sum_{L_c} [I_{CBS}(\lambda_i, k\theta_j; L_c) - I(\lambda_i, \theta_j; L_c)]^2$$

FIG. 1-11

$$J_{m,n} = \frac{\partial I_{CBS}(\lambda_j, k\theta_j; L_c)}{\partial x_n}$$

FIG. 1-12

$$y_m = I(\lambda_j, \theta_j; L_c) - I_{CBS}(\lambda_j, k\theta_j; L_c)$$

FIG. 1-13

$$p(\theta) = \frac{4(1-2pb)}{\langle \theta^2 \rangle} \exp\left(-\frac{\theta^2}{\langle \theta^2 \rangle}\right) + 2pb$$

FIG. 1-14

$$I(\rho;z) = \frac{1}{(2\pi)^2} \mu_S(z) pb(z) \exp\left[-2\int_0^z \mu_T(\xi) d\xi\right]$$
$$\times \int d\kappa \exp(i\kappa \cdot \rho) \left\{ \exp\left[2\int_0^z \mu_S(z-\xi) X(\kappa\xi, z-\xi) d\xi\right] - 1\right\}$$

FIG. 1-15

$$I_{CBS}(q_\perp;z) = \frac{2\pi f}{kL} \int_{-\infty}^{\infty} dx I(|x|;z) \exp[iq_\perp x] \text{sinc}[x/L_c]$$

FIG. 1-16

$$I_{CBS,l}(q_\perp) = \frac{2\pi f}{kL} \int_{-\infty}^{\infty} dx I_l(|x|) \exp[iq_\perp x] \text{sinc}[x/L_c]$$

FIG. 1-17

$$F(x) = \frac{1}{2} \sum_{i=1}^{N_\theta} \sum_{L_c} [I_{CBS}(k\theta_i;L_c) - \mathcal{I}(\theta_i;L_c)]^2$$

FIG. 1-18

$$J_{m,n} = \frac{\partial I_{CBS}(k\theta_i;L_c)}{\partial x_n}$$

FIG. 1-19

$$y_m = \mathcal{I}(\theta_i;L_c) - I_{CBS}(k\theta_i;L_c)$$

FIG. 1-20

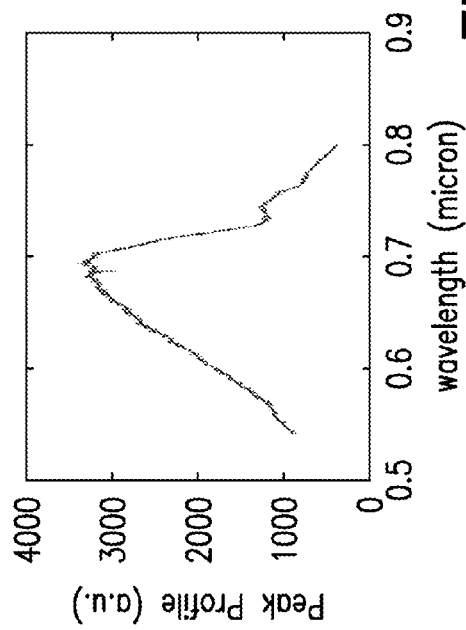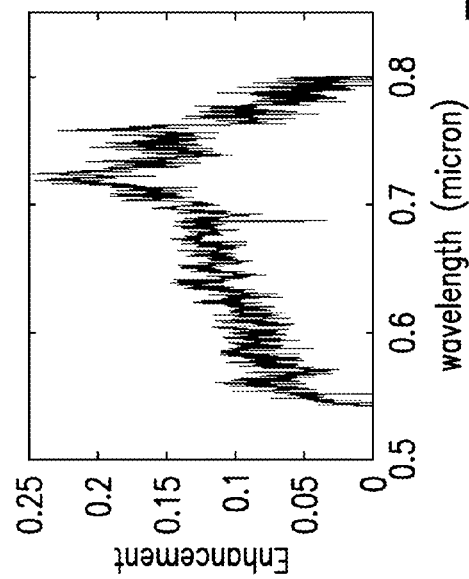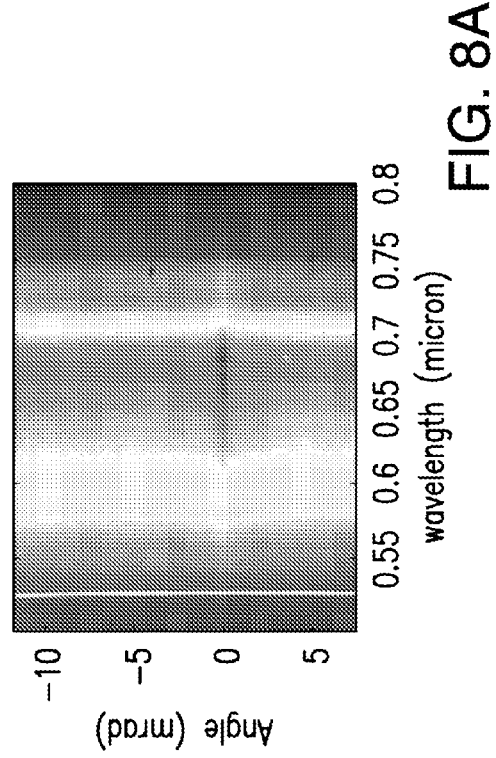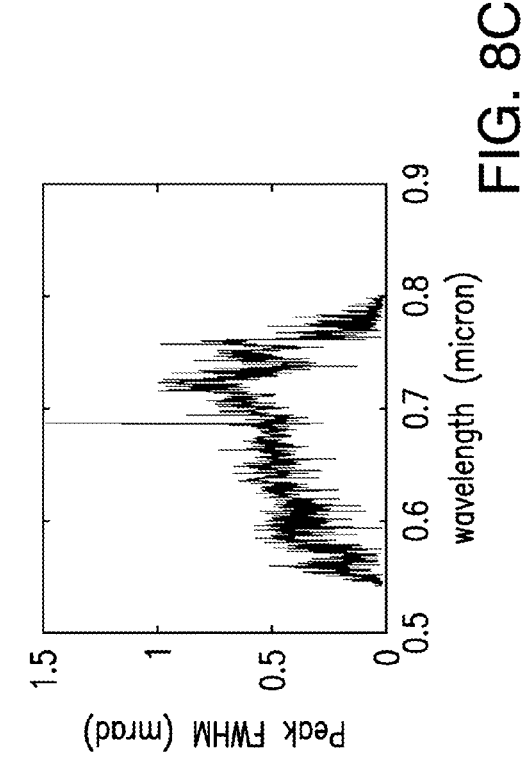

LOW COHERENCE ENHANCED BACKSCATTERING TOMOGRAPHY AND TECHNIQUES

CROSS-REFERENCE TO RELATED APPLICATIONS

This application is a U.S. National Stage application of International Patent Application No. PCT/US2011/036744 filed May 17, 2011, which claims priority to U.S. Ser. No. 61/347,663 filed May 24, 2010. Both of these applications are incorporated by reference in their entireties.

FIELD OF THE DISCLOSURE

This disclosure relates to biophotonics or biomedical optics, and more particularly to characterization of the superficial layer of tissue using low coherence enhanced backscattering of light.

BACKGROUND OF THE DISCLOSURE

Histopathological examination of tissue has been an essential component of pathology. Current knowledge about carcinogenesis, cancer diagnostics and prognostication is predominantly based on histological study on tissue, cells and nuclei. Morphometric information, especially nuclear morphometry, has been shown to have great potential in assisting cancer screening, diagnosis, grading and classification, prognosis, analysis of angiogenesis, and evaluating the efficacy of therapy.

Traditional histopathological examination has several limitations, including: (1) it can only acquire the two dimensional information from the cells or nuclei of interest; (2) it is qualitative or semi-quantitative; (3) it requires tissue excision and processing for examination; and (4) it is frequently subject to the inter- and intra-personal variability in interpretation, thus with a relatively low reproducibility. Digital morphometric techniques were introduced to overcome these problems. Digital morphometry helps improve the reproducibility of histological examination, but its clinical utility is yet to be proven. Better segmentation (the delimitation of boundaries between two compartments) and comprehensive examination of the entire cell has been found to be crucial for yielding reproducible and convincing results. Three-dimensional (3D) stereological methods have recently been introduced in clinical diagnostics and are proving to be beneficial.

The majority of human cancers (nearly 90%) arise from the epithelial cells that line many organs. In dysplastic epithelial tissue, dysplastic epithelial cells differ from normal ones in their shapes and the size of their nuclei. A variety of optical spectroscopic and imaging methods can be used to detect abnormal changes in light scattering and absorption properties of tissue to detect carcinogenesis. However, to detect cancer in its earliest stage (precancer) it is crucial to depth-selectively probe the specific areas that are initially involved in neoplastic transformations (e.g. the base of the crypt for colon carcinogenesis). It therefore is highly desirable to reliably and accurately image epithelial cells and their nuclei at various depths.

Current approaches such as diffuse optical tomography (DOT) suffer from poor spatial resolution (5-10 millimeters) due to light diffusion. Other approaches such as Optical Coherence Tomography (OCT) have yielded micrometer resolution and cross-sectional imaging. This permits the imaging of tissue microstructure in situ, yielding micronscale resolution image with use of low temporal coherence light. However, it is difficult for OCT to image structures such as nuclei for various technical reasons.

It is desirable to combine the advantages of both techniques: (1) the sensitivity to nuclear morphology and cellular structure of light scattering, and (2) the high spatial resolution offered by low coherence light, to perform high resolution imaging of the structure and composition of tissue. This would provide a 3D image of the nuclear morphology and cellular structure for tissue in real time, with no tissue excision or processing required.

SUMMARY OF THE DISCLOSURE

The present disclosure describes a method for depth-selective sensing of the superficial layer of tissue. In accordance with the disclosure, a 3D tomographic tool images the microarchitecture and molecular conformation of the superficial layer of tissue. The method, referred to herein as low coherence enhanced backscattering tomography (LEBT), combines the high resolution advantage of low coherence light and the high sensitivity advantage of light scattering to tissue structure and composition, and furthermore offers the following advantages:

Intact tissue can be examined without the need of excision or processing.

It can be applied in in situ measurements.

It is capable of generating 3D images of the nuclear morphology and cellular structure for the superficial layer of the tissue. This is particularly useful in detecting cancer and precancer at the earliest stage of carcinogenesis.

According to embodiments of the disclosure, a method for noninvasive imaging of a tissue sample includes the steps of illuminating a location on a surface of the sample using an incident beam of partially spatially coherent light characterized by a variable spatial coherence length $L_c$; detecting low coherence enhanced backscattered (LEBS) light characterized by a scattering angle $\theta$; obtaining LEBS spectra characterized by light intensity versus light wavelength $\lambda$ for a given scattering angle $\theta$ and a given coherence length $L_c$; recording two-dimensional (2D) images, each based on spectra corresponding to a different coherence length $L_c$; scanning the incident beam across the surface to record a plurality of 2D images; forming a data set of the recorded 2D images; and constructing a three-dimensional (3D) image of the sample from the data set.

The foregoing has outlined, rather broadly, the preferred features of the present disclosure so that those skilled in the art may better understand the detailed description of the disclosure that follows. Additional features of the disclosure will be described hereinafter that form the subject of the claims of the disclosure. Those skilled in the art should appreciate that they can readily use the disclosed conception and specific embodiment as a basis for designing or modifying other structures for carrying out the same purposes of the present disclosure and that such other structures do not depart from the spirit and scope of the disclosure in its broadest form.

BRIEF DESCRIPTION OF THE DRAWINGS

FIGS. 1-1 to 1-20 show formulas that are used in analysis of low-coherence enhanced backscattering (LEBS) spectra to construct an image of a layer of tissue.

FIG. 4 illustrates an arrangement for obtaining LEBS spectra.

FIG. 5 is a flowchart illustrating a LEBT procedure for imaging a homogeneous medium based on an LEBS signal, in accordance with an embodiment of the disclosure.

FIG. 6 is a flowchart illustrating a LEBT procedure for imaging a multilayer medium based on an LEBS signal, in accordance with an another embodiment of the disclosure.

FIG. 7 is a flowchart illustrating a LEBT procedure for imaging a multilayer medium based on an LEBS signal, in accordance with a further embodiment of the disclosure.

FIGS. 8A-8D show measured data, from a procedure embodying the disclosure, for a cancerous tissue site.

FIG. 10 shows measured data comparing the enhancement factor for the cancerous tissue site of FIGS. 8A-8D with the adjacent normal tissue site of FIGS. 9A-9D.

DETAILED DESCRIPTION

LEBT and Biomedical Imaging

A LEBT technique according to the disclosure can image intact biological tissues at the microscopic scale ex vivo and in vivo based on optical contrast, extending LEBS to a three dimensional (3D) tomographic imaging modality. By detecting only low-order backscattering light via spatial coherence gating, LEBT solves the low spatial resolution problem due to light diffusion and achieves excellent depth selection. At the same time, low-order scattering light is sensitive to the microarchitecture and the molecular conformation of biological tissues, relating to physiological states such as the morphological alteration due to carcinogenesis and the oxygenation of hemoglobin.

Epithelial tissues have a multi-layered structure composed of a superficial cellular layer (epithelium) with a characteristic thickness of ~100 μm. The main characteristics of light propagation in a turbid medium can be summarized by a set of length scales: the scattering mean free path, $l_s=1/\mu_s$, the mean distance between consecutive scattering events; the transport mean free path, $l_t=l_s/(1-g)$, the characteristic distance over which the memory of the initial propagation direction gets lost; and the absorption length, $l_a=1/\mu_a$, the characteristic length for light absorption. Here $\mu_s$, $\mu_a$ are the scattering and absorption coefficients, respectively, and g is the mean cosine of light scattering angles (the anisotropy factor). Typical values for tissues scattering light in the visible and near-infrared wavelength range satisfy $l_a \gg l_t \gg l_s$ and $g \geq 0.9$.

Light Scattering By Cells and Tissue

The penetration depth of backscattered light is determined by the phase function of light scattering in the medium, the polarization and coherence state of the incident beam, and the collection condition of the detector. To detect cancer at the earliest stage, it is crucial to depth selectively probe the superficial layer of tissue, the mucous layer about 100 μm below the surface, where most cancer initiates by controlling the penetration depth of light.

Figure 2A:
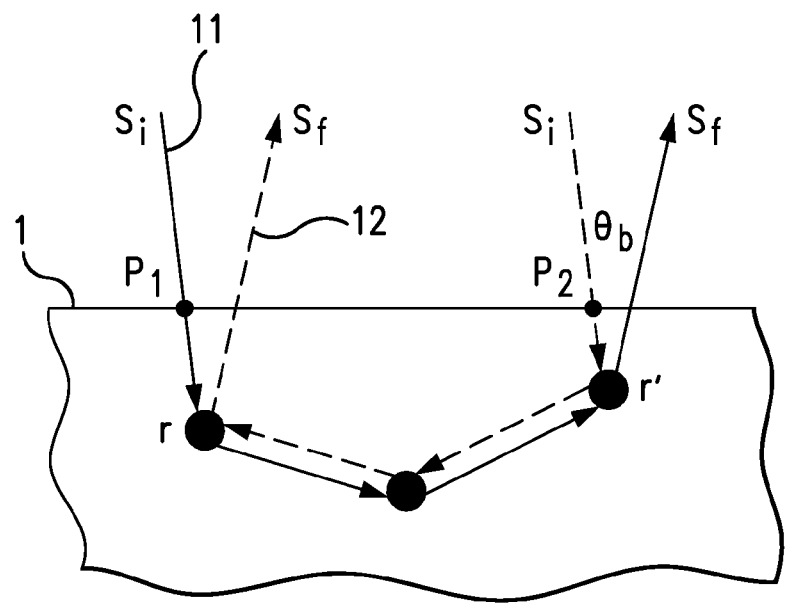
FIG. 2A schematically illustrates a scattering path for light incident on a superficial layer of tissue.

Low coherence enhanced backscattering (LEBS) achieves depth selection through spatial coherence gating. Enhanced backscattering is a reported phenomenon of multiple scattering light where the backscattered light is found to enhance around the exact backscattering direction. This enhancement of light intensity results from constructive interference between two amplitudes of a coherent wave propagating through a scattering medium along the same path but with one in reverse order of the other. FIG. 2A shows a scattering path 11 and its time-reversal conjugate 12 incident in the direction s, and escaping the medium in the direction $s_f$. The angle between the paths is $\theta_b$, and $P_{1,2}$ is the incident point of light on the surface 1 of a sample. The time-reversed path 12 is $q_b \cdot (r'-r)$ longer than the forward path 11, where $q_b=k(s_i+s_f)$, $k=2\pi/\lambda$ is the wave vector, and $\lambda$ is the wavelength of the incident light.

Figure 2B:
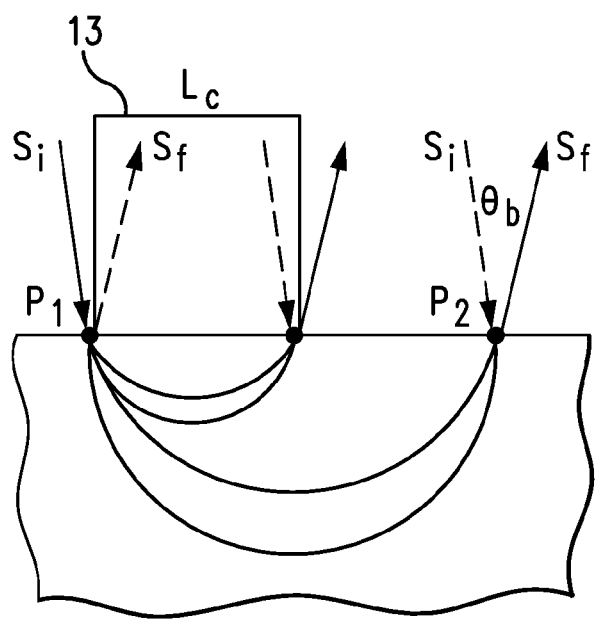
FIG. 2B schematically illustrates a scattering path for light from a partially spatially coherent light source incident on a superficial layer of tissue.

As shown in FIG. 2B, a partially spatially coherent source with a coherence length $L_c$ introduces an additional phase correlation at the illumination points $P_1$ and $P_2$. The photons participating in constructive interference must be low order scattered and reside within the coherence area 13 of size $L_c$. The penetration depth of low coherence enhanced backscattering light is hence significantly shortened, and controlled to be on the order of $L_c$ when $L_c$ is shortened to less than one scattering mean free path $l_s$.

The behavior of the propagation of light in highly scattering media such as tissue is determined by the phase function $p(\theta)$ of light scattering in the medium. After a sufficient number of scattering events, light migration approaches diffusion that can be simply characterized by one parameter: the transport mean free path, $l_t$, which depends only on the first moment of the phase function. The situation is very different for low-order scattered photons; all the moments of the phase function will affect the behavior of low-order scattered photons. Monte Carlo simulations have repeatedly observed the significant influence of higher order moments of the phase function on the profile of backscattered light close to the incident beam exactly where low-order scattered photons dominate. This suggests that the accurate model of single scattering property of the scatterers is crucial for imaging with low-order scattered photons.

Scattering structures of a wide size distribution inside a cell, including nuclei, mitochondria and organelles, contribute to light scattering by a cell. The finite difference time domain (FDTD) method has been used to compute light scattering by a cell taking into full account of its complex internal structure. The FDTD method is, however, time prohibitive for routine applications in characterizing biological cells and tissues from light scattering measurements. The Mie model remains the most popular choice due to its simplicity, although the deficiency of the Mie model has been manifested by many recent studies. It has been found that the size of scattering centers obtained using the Mie model alone is too small to account for either the cell or the nucleus.

Both nuclear Mie scattering and background fractal scattering are important to describe correctly light scattering by biological cells inside tissue. The nuclear Mie scattering component alone underestimates the probability of large angle light scattering by two orders of magnitude. Light scattering by biological cells (scattering coefficient $\mu_s$ and phase function $p(\theta)$) in tissue contains both nuclear Mie and background fractal components. An expression for $\mu_s p(\theta)$ is shown in FIG. 1-1. The nuclear Mie component phase function $p_{Mie}$ determines the behavior of small angle scattering, while the background fractal component phase function $p_{hg}$ determines the behavior of large angle scattering.

Analysis of Low Coherence Enhanced Backscattering

The LEBS signal can be found from the Fourier transform of the radial profile $I(\rho)$ of incoherent backscattered light and is given by the expression in FIG. 1-2. In this expression, $q\perp \sim k\theta_b$, $k=2\pi/\lambda$ is the wave vector with the wavelength of light, $\theta_b$ is the angle between the incident and outgoing directions, and $J_0$ and $J_1$ are the Bessel functions of the first kind of order 0 and 1, respectively. The portion of the radial profile within $\rho<3L_c$ of $I(\rho)$ will determine the main feature of LEBS. The case of particular relevance for LEBS is when the coherence length $L_c$ is less than the scattering mean free path $l_s$.

Figure 3A:
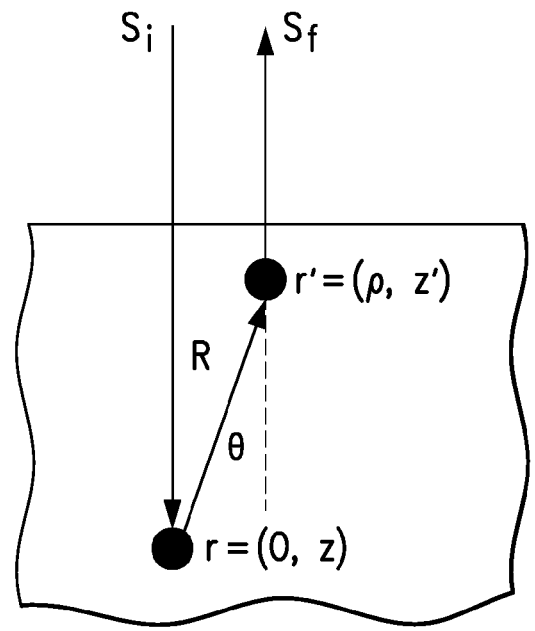
FIG. 3A schematically illustrates a light scattering path including double scattering with one large-angle scattering and one small-angle scattering.
Figure 3B:
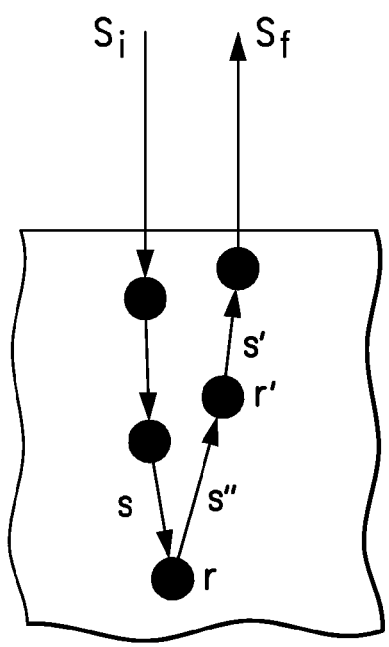
FIG. 3B schematically illustrates a light scattering path with one large-angle scattering and multiple small-angle scattering.

The incoherent backscattered light remitted at the distance $\rho<l_s$ from the point of incidence is dominated by double scattered photons which experience exactly one small angle scattering and one large angle scattering. Photons which experience multiple small angle scattering and exactly one large angle scattering are important in the case of $L_c<l_s$. FIG. 3A illustrates a scattering light path where photons experience double scattering with one small angle and one large angle scattering; FIG. 3B illustrates a scattering light path where photons experience multiple small angle scattering and exactly one large angle scattering before escaping the medium in the backscattering direction.

Referring to the two scattering events shown in FIG. 3A, based on the nature of scattering by biological cells where nuclear Mie scattering dominates forward scattering and background fractal scattering dominates large angle scattering, it follows that the scattering with a small angle $\theta$ is associated with nuclear Mie scattering while the scattering with an angle of ~180° is associated with background fractal scattering. For LEBS in tissue in the exact backscattering direction ($q\perp=\theta=0$), a simple expression for the LEBS spectra $I_{CBS}(\lambda)$ has been obtained, as shown in FIG. 1-3.

Light scattering by cells in tissue contains both nuclear Mie scattering and background fractal scattering by the subcellular structures of small sizes. Fitting the LEBS spectra to the equation of FIG. 1-3 provides information on both Mie and fractal scatterers. Nuclear Mie scattering dominates small angle light scattering and has a characteristic Mie oscillatory pattern in its wavelength dependence. Background fractal scattering dominates large angle light scattering and has a power law dependence on wavelength. Mie and fractal scattering influence the LEBS spectrum distinctively. Accordingly, low coherence enhanced backscattering can be used to extract the characteristics of both the nuclear morphology and the cellular structure.

LEBT Apparatus

Figure 4:
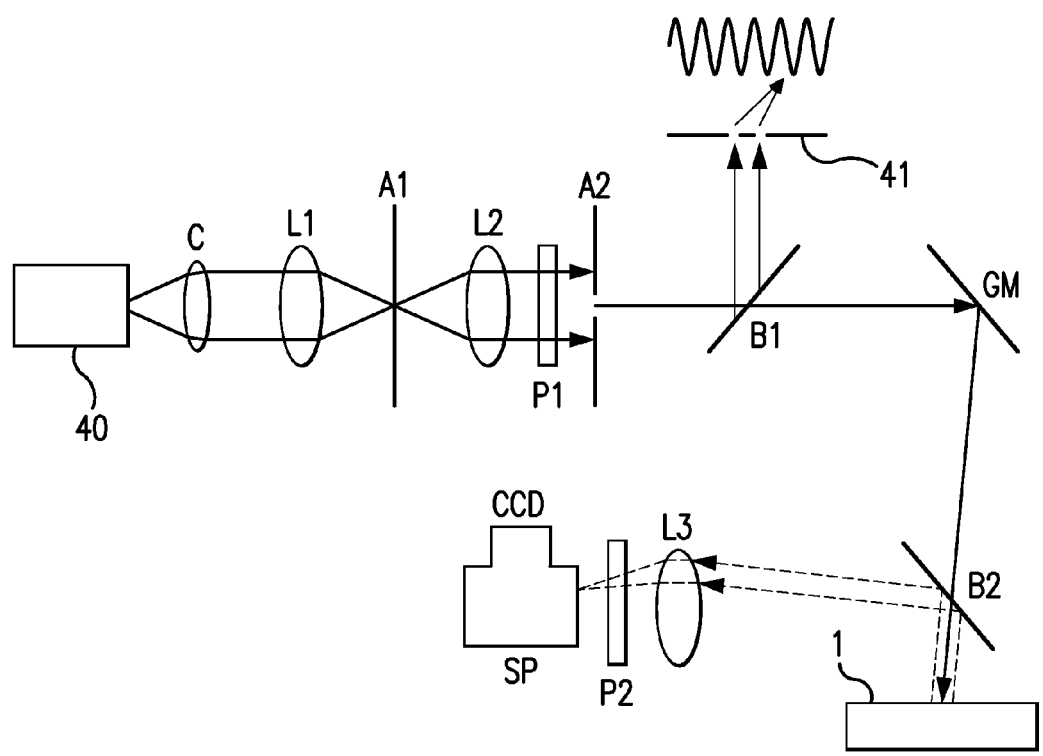

An experimental arrangement for imaging a tissue sample by LEBT is shown in FIG. 4. Light source 40 in this arrangement is a 75 W xenon lamp. Light from source 40 passes through condenser C, lens L1, apertures A1, lens L2, polarizer P1, aperture A2, and beamsplitter B1; the light reflects from galvanometer mirror GM, passes through beamsplitter B2, and is incident on the sample surface 1. The spatial coherence length, $L_c$, of the illumination light is varied in the range of 20 μm-200 μm by adjusting the aperture size of aperture A1 and monitored by interference through double slit 41. The light backscattered by the sample is collected by a Fourier lens L3, a polarizer P2, and an imaging spectrograph SP. The two polarizers P1 and P2 are both oriented in the horizontal direction and hence the parallel-polarized backscattered light is detected. The entrance slit of the imaging spectrograph is positioned at the focal plane of the lens L3. The spectrograph disperses light in the direction perpendicular to the slit according to the wavelength. As a result, light backscattered by the sample at different scattering angles (−5° to 5°) and of different wavelengths (400-700 nm) is recorded at different pixels on a CCD. Setting the angle of incidence of the incident beam to be ~10° ensures that the specular reflected light by the sample will not be detected by the camera.

The galvanometer mirror GM scans the incident beam across the surface of the sample (this scan is referred to below as B-scan). At each scanning position, the CCD records a series of 2D images, $I(\lambda,\theta;L_c)$ (that is, light intensity I versus wavelength λ and scattering angle θ), for enhanced backscattered light of varying penetration depth into the sample by controlling the spatial coherence length $L_c$ of the incident beam through adjusting the aperture size of A1 (this scan is referred to below as A-scan).

The arrangement of FIG. 4 is shown as an example. Other experimental arrangements for scanning light across a sample surface and detecting light backscattered from the surface will be apparent to those skilled in the art.

The recorded 2D image $I(\lambda,\theta;L_c)$ is normalized according to $[I(\lambda,\theta;L_c)-I_{base}(\lambda)]/I_{ref}(\lambda)$ where $I_{base}(\lambda)$ is the baseline scattering intensity measured at large scattering angles $\{\theta>5°\}$ and $I_{ref}(\lambda)$ is the reference intensity collected from a reflectance standard. This normalization procedure compensates for the nonuniform spectrum of the xenon lamp illumination and the spectral response of the detector. The resulting LEBS signal will be denoted as a 2D array $\tilde{I}(\lambda_i, \theta_j; L_c)$ where $\lambda=\lambda_i$ and $\theta=\theta_j$ for $i=1,2,3,\ldots,N_\lambda$ and $j=1,2,3,\ldots,N_\theta$ where $N_\lambda$ and $N_\theta$ are the number of the wavelengths and the scattering angles sampled, respectively. The number of spatial coherence lengths for the source used in one A-scan is $N_{Lc}$.

A 3D image of the superficial layer of the sample is reconstructed from the recorded data set.

LEBT Model For Imaging Homogeneous and Stratified Media

The LEBS signal $I_{CBS}$ relates to the Fourier transform of the radial profile $I(\rho)$ of incoherent backscattered light and is determined by the portion of the radial profile $I(\rho)$ within $\rho<3L_c$ under illumination of partially spatially coherent light. Thus, LEBS photons must turn around 180° in total through a series of scattering events inside the medium and emerge at the very proximity of the point of incidence ($\rho<3L_c<l_s$ in typical LEBS applications).

Regarding epithelial and other biological cell light scattering, it has been observed that (1) light scattering contains both nuclear Mie and background fractal components; (2) the phase function $p(\theta)$ decays exponentially away from the exact forward direction at small scattering angles θ, then decays more slowly at larger scattering angles, and increases slightly as the scattering angle approaches 180°; and (3) the probability of forward scattering is ~$10^6$ times greater than the probability of scattering into 80°-180°. From these observations, it may be inferred that the dominant contribution to the low coherence enhanced backscattering light inside biological materials comes from the photons which have been scattered exactly once with a large scattering angle ~180° and have experienced one or more small angle scattering events. Enhanced backscattering photons thus experience at least double scattering, with one large-angle event; the exact sequence of scattering events is irrelevant. Photons experiencing only small angle scattering escape the medium at $\gg l_s$ away from the point of incidence and will not contribute to LEBS.

A derivation of an expression for $I(\rho)$ for a uniform medium, where ρ is the scattering vector (see FIG. 3A), using Green's function analysis techniques, has been previously reported. This expression is shown in FIG. 1-4, where: z is the penetration depth; $\mu_{s,bg}$ and $\mu_{s,Mie}$ are the background fractal and nuclear Mie component scattering coefficients respectively; $p_{bg}$ is the phase function due to background refractive index fluctuation; $\mu_T=\mu_{s,Mie}+\mu_{s,bg}+\mu_a$ with $\mu_a$ being the attenuation coefficient; and $\chi_{Mie}(\kappa\xi)=2\pi_0\int^\infty P_{Mie}(\theta)J_0(\kappa\xi\theta)\theta d\theta$ is the Fourier transform of the nuclear Mie component phase function. The expression of FIG. 1-4 contains contributions from backscattered light which has been scattered at least twice. Single scattering does not contribute to enhanced backscattering and is not included in the expression of FIG. 1-4.

It has also been shown that the nuclear Mie component phase function may be approximated as $p_{Mie}(\theta) \sim 4J_1^2(\theta x)/\theta^2$ where $x=k\alpha$ is a size parameter and $\alpha$ is the mean radius of the nucleus.

The detected LEBS spectral intensity $I_{CBS}(\lambda, q\perp)$, under illumination of partially spatially coherent light of wavelength $\lambda$ and a spatial coherence length $L_c$, is a superposition of signals from layers at different depths $z$; an expression for this intensity is shown in FIG. 1-5. Inside a uniform medium, the contribution from a layer at depth $z$ is given by the expression in FIG. 1-6 (wherein H is the Heaviside function). The peak of the LEBS spectra is obtained from this expression by setting $q\perp=0$. The penetration depth of the LEBS light is given by the expression in FIG. 1-7.

Imaging Homogeneous and Stratified Media: Reconstruction Procedures

According to an embodiment of the disclosure, a procedure for reconstructing a 3D image of the superficial layer of a tissue sample from the recorded data set of 2D images is detailed below.

The nuclear structure and cellular environment is represented by the mean nuclear radius a, the scattering power of the background refractive index fluctuation b, the nuclear number density $N_{Mie}$, and the nuclear-cellular (N/C) scattering ratio $c=N_{Mie}\pi\alpha^2/A$, where A is a constant relating to the strength of the refractive index fluctuation. The reconstruction is first performed for the depth profile of a, b, $N_{Mie}$, and c at the illuminated point (A-scan), and the complete 3D image of the sample is obtained by scanning the incident beam across the surface of the sample (B-scan).

For one A-scan, a set of LEBS spectra $\tilde{I}(\lambda_i, \theta_j; L_c)$ at the scattering angle $\theta_j$ under illumination of partially spatially coherent source of wavelength $\lambda_i$ and of varying spatial coherence length $L_c$ is be measured. The wavelength $\lambda_i$ (i=1,2, 3, ..., $N_\lambda$) covers the visible spectral range, the scattering angle $\theta_j$(j=1,2,3, ..., $N_\theta$) is from ~–5° to ~5° with a step size of 0.1°, and a series of total $N_{Lc}$ spatial coherence lengths $L_c$ are from ~20 μm to ~200 μm with a step size ~20 μm.

Figure 5:
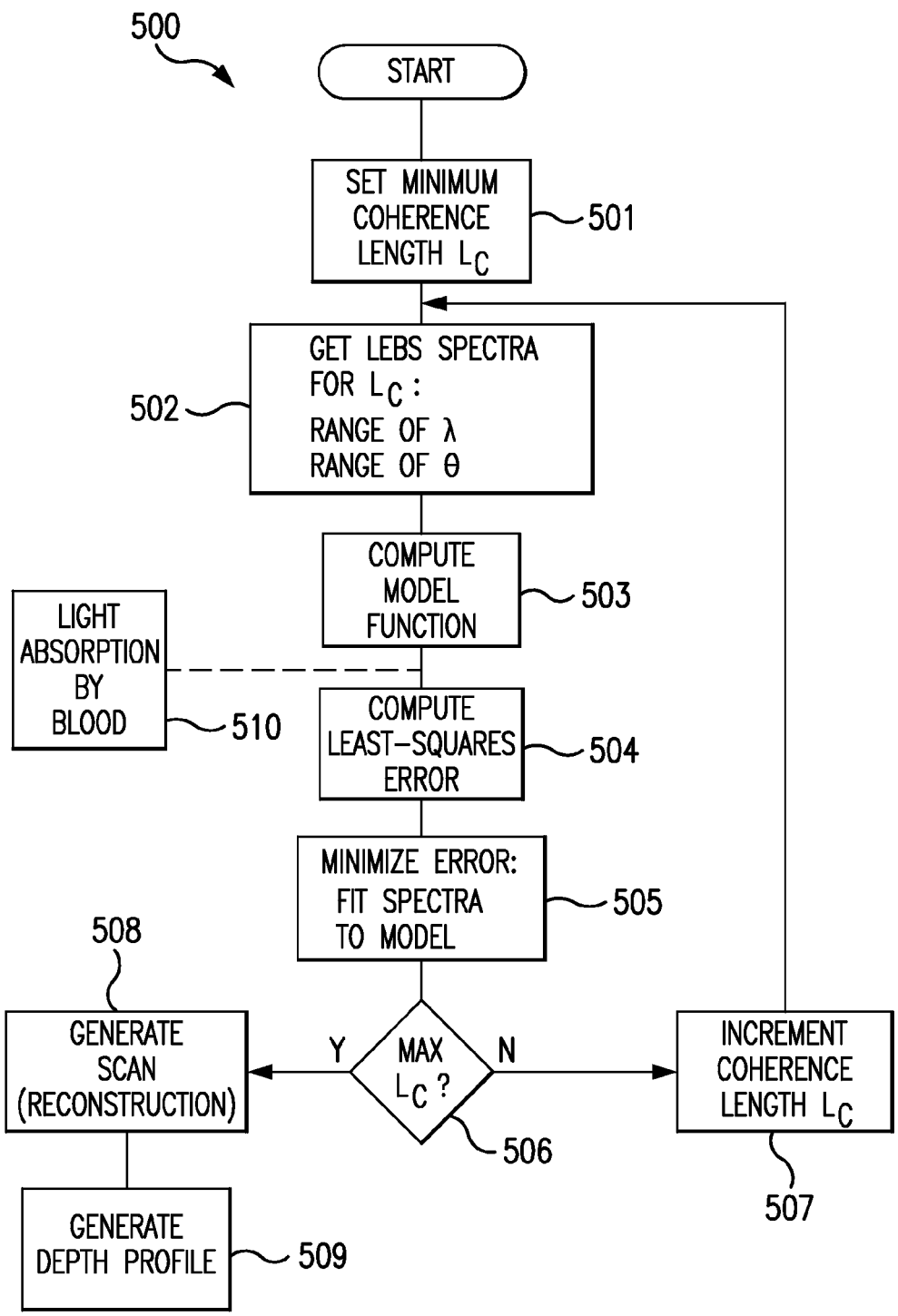

In an embodiment, a reconstruction procedure 500 for one A-scan is shown in the flowchart of FIG. 5. In step 501, the spatial coherence length $L_c$ is set to its minimum value (typically 20 μm, as noted above). The LEBS spectra for the $N_\lambda$ wavelengths and $N_\theta$ angles are retrieved from the data set (step 502). A model function $I_{CBS}(\lambda_i, k\theta_j; L_c)$ is computed using the expressions of FIGS. 1-5 and 1-6, with the wavelength set to $\lambda_i$ and the spatial coherence length set to $L_c$ (step 503). In step 504, a least-squares error function $f(a, b, N_{Mie}, c)$ is computed using the expression in FIG. 1-8. A known optimization procedure is then used to minimize this error (step 505) for the nuclear radius a, the scattering power b, the nuclear number density $N_{Mie}$, and the N/C scattering ratio c, thus fitting the LEBS spectra to the model function. If the end of the range of $L_c$ values has not been reached (step 506), then $L_c$ is incremented by one step, and the above procedure is repeated (step 507). After all spectra for the various $L_c$ have been fitted, an A-scan of LEBT is generated (step 508) which in turn (step 509) gives the depth profile of the nuclear radius a, the scattering power b, the nuclear number density $N_{Mie}$, and the N/C scattering ratio c with respect to the penetration depth $z_{max}$ given by the expression in FIG. 1-7.

In another embodiment, the LEBS light absorption by blood 510 is no longer treated as negligible. The error function therefore has as additional arguments $c_{Hb}$ and $C_{HbOb}$, the concentrations of deoxy- and oxy- hemoglobin respectively. These concentrations are fitted in addition to the above-mentioned parameters in the error minimizing procedure.

Figure 6:
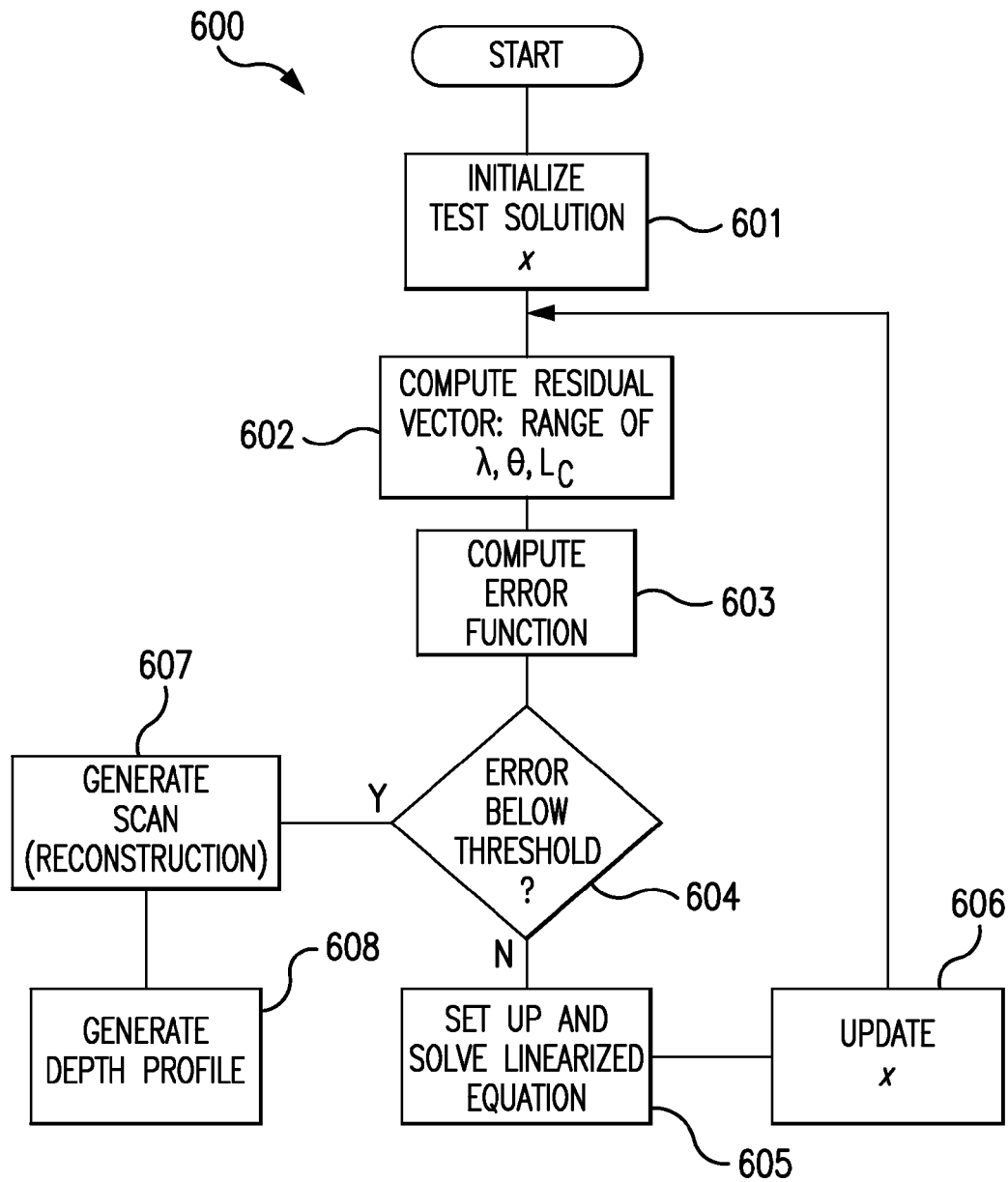

According to a further embodiment, the sample is assumed to be stratified, and the LEBS signal is written as a summation of multiple discrete layers. If there are a total of $N_z$ layers with depth (n-1)$\Delta z \le z \le n\Delta z$ for n=1,2,3, ..., $N_z$ and $\Delta z$ is the thickness of one layer, the LEBS signal for the stratified medium is given by the expression in FIG. 1-9. The signal from the lth layer is given by the expression in FIG. 1-10, where the superscript l indicates a quantity associated with the lth layer. The procedure used in this embodiment is shown in the flowchart of FIG. 6.

In procedure 600, the solution fitting the LEBT reconstruction and depth profile is given by a vector x that minimizes the error function F(x) as shown in FIG. 1-11. There are N=6$N_z$ elements in x; that is, a, b, $N_{Mie}$ $c_{Hb}$ and $C_{HbOb}$ for each of the layers in the sample. The nth element of x is labeled $x_n$ where $1 \le n \le N$. The total number of data points is M=$N_\lambda N_\theta N_{Lc}$. The Jacobian J is an M×N matrix with elements $J_{m,n}$ given by the expression in FIG. 1-12, and where m $\equiv$(ij$L_c$).

In step 601, an initial value for x is assigned, either as a guess from previously available information or a result from procedure 500. In step 602, a residual vector y is computed; elements of y are given by the expression in FIG. 1-13. The error function is then evaluated (step 603) in terms of vector y: F(x)=½ $y^T y$ where $y^T$ is the transpose of y.

If this result for F(x) is less than the predefined error threshold (step 604), then the current x is the desired solution. Otherwise, the Jacobian J is computed, and the linearized equation J $\Delta x$=y is solved for $\Delta x$ (step 605). The test solution x is then updated (step 606) to x+$\Delta x$, and the procedure is repeated at step 602 with computation of a new residual vector. Once a solution x below the error threshold is found, an A-scan of LEBT for the stratified sample is generated (step 607) which in turn (step 608) gives the depth profile.

The lateral resolution of LEBT is determined by the spot size of the beam incident on the sample. As the spot size is reduced to ~$L_c$, the speckle becomes appreciable; the lateral resolution of LEBT is thus limited by a tradeoff between resolution enhancement and speckle suppression. The optimal value for the spot size has been found to be approximately $3L_c$. The axial resolution of LEBT with procedure 600 depends on the layer thickness $\Delta z$; $\Delta z$ may be set at ≤10 μm.

A 3D LEBT image of the sample is obtained by combining imaging from the A-scan (that is, 2D images at the point of illumination for varying penetration depths) with the B-scan (scanning of the incident beam across the surface of the sample). This 3D image has both morphometric (nuclear size, nuclear number density, cellular scattering power, nuclear/cellular scattering ratio) and oxygenation (concentrations of deoxy- and oxy-hemoglobin) components. An axial resolution of ~10 μm may be obtained. Since the typical thickness of the epithelium is ~100 μm, LEBT as described above is effective to image the epithelium or the epithelium plus the underlying vascularized stroma, which are most diagnostic of tissue health.

Alternative LEBT Model For Imaging Stratified Media

As noted above, the LEBS signal $I_{CBS}$ relates to the Fourier transform of the radial profile I($\rho$) of incoherent backscattered light and is determined by the portion of the radial profile $I(\rho)$ within $\rho<3L_c$ under illumination of partially spatially coherent light. Thus, LEBS photons must turn around 180° in total through a series of scattering events inside the medium and emerge proximate to the point of incidence. In this model, the coherence length $L_c$, is in the range given by $\rho<3L_c<l_s$; the profile $I(\rho)$ depends critically on the details of the phase function $p(\theta)$.

Tissue contains scatterers of various sizes: smaller than, comparable with, and larger than the wavelength of visible light. Light scattering in tissue is predominantly in the forward direction. The scattering function of tissue may be viewed as having two components: the first within the forward scattering angles and originating from light interaction with large scatterers such as nuclei, and the second for large scattering angles due to light scattering by smaller structures. Assuming that the small-angle scattering function takes a Gaussian form and the large-angle scattering is isotropic, the phase function may be written as in FIG. 1-14, where $<\theta^2>$ is the mean squared scattering angle and $p_b$ depends on the ratio of the strength of light scattering into larger angles (>5°) to that into smaller angles (<5°). The phase function is normalized to $\frac{1}{2}\int_0^\pi p(\theta) \sin \theta d\theta = 1$. For large soft particles such as nuclei with a relative refractive index close to unity, the phase function at angles close to the forward direction may be approximated by $p(\theta) \sim 4J_1^2(\theta\sigma)/\theta^2 \sim \sigma^2 \exp(\sigma^2\theta^2/4)$, where $\sigma=k\alpha$ is the size parameter of the scatterer and $\alpha$ is the radius of the particle. The mean squared scattering angle $<\theta^2>$ is thus related to the size parameter $\sigma$ by $<\theta^2>=4/\sigma^2$.

In this LEBS model, the tissue is treated as having multiple discrete layers, and the intensity of the LEBS signal due to scattering at a radial distance $\rho$ at depth z is written as $I(\rho;z)$. The backscattering intensity is thus $I(\rho)=\int_0^\infty dz\, I(\rho;z)$, where the contribution from depth z to the backscattered light at the radial distance $\rho$ is given by the expression in FIG. 1-15. In this expression, $\mu_T(z)=\mu_s(z)+\mu_a(z)$ with $\mu_T$ being the attenuation coefficient, and $\mu_s$ and $\mu_a$ the scattering coefficient and the absorption coefficient respectively; and $\chi$ is the Fourier transform of the phase function at the depth z.

The expression of FIG. 1-15 includes contributions from backscattered light which has been scattered at least twice. Single scattering does not contribute to enhanced backscattering.

The intensity of the LEBS signal, $I_{CBS}(q\perp;z)$, is a superposition of signals from layers at different depths. Referring to FIG. 4, in this model the light source is treated as a line source where slit A1 is placed on the Fourier plane with respect to lenses L1 and L2, the slit has width w and height L, and the focal length of lens L2 is $f$. The LEBS signal $I_{CBS}(q\perp;z)$ is then given by the expression in FIG. 1-16, where $\text{sinc}(x) \equiv \sin(x)/x$ and it is assumed that w, $L_c \ll L$. The peak of the LEBS spectra is obtained by setting $q\perp=0$.

The detected LEBS spectra $I_{CBS}(q\perp)$ under illumination of partially spatially coherent light of wavelength $\lambda$ and a spatial coherence length $L_c$ is a superposition of signals from the layers at different depth z. The penetration depth of the LEBS light is given by the expression in FIG. 1-7.

Reconstruction Procedure For a Stratified Sample

According to a further embodiment, the sample is assumed to be stratified, and the LEBS signal is written as a summation of multiple discrete layers. If there are a total of $N_z$ layers with depth $(n-1)\Delta z \leq z \leq n\Delta z$ for $n=1,2,3,\ldots, N_z$ and $\Delta z$ is the thickness of one layer, the LEBS signal for the stratified medium is given in FIG. 1-9 for a given wavelength $\lambda$. If the sample is probed at wavelength $\lambda$, the signal from the lth layer is given by the expression in FIG. 1-17.

Figure 7:
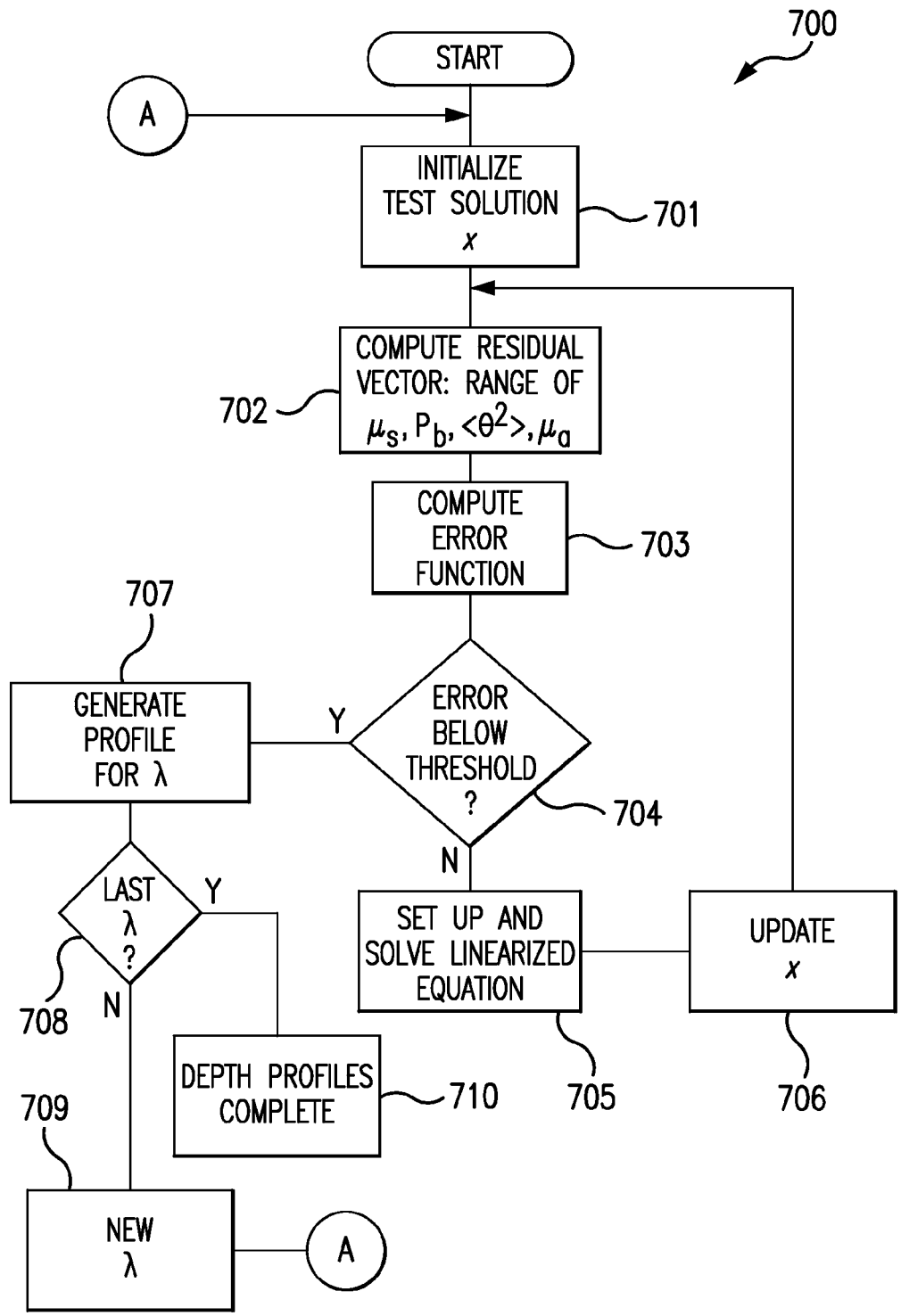

A procedure to reconstruct the depth-resolved profile of $\mu_s$, $p_b$, $<\theta^2>$, and $\mu_a$ at one probing wavelength $\lambda$, in accordance with this embodiment, is shown in the flowchart of FIG. 7. In procedure 700, the solution fitting the LEBT reconstruction and depth profile is given by a vector x that minimizes the error function $F(x)$ as shown in FIG. 1-18. There are $N=4N_z$ elements in x; that is, $\mu_s$, $p_b$, $<\theta^2>$, and $\mu_a$ for each of the layers in the sample. The nth element of x is labeled $x_n$ where $1 \leq n \leq N$. The total number of data points is $M=N_{\theta NLc}$. The Jacobian J is an M×N matrix with elements $J_{m,n}$ given by the expression in FIG. 1-19, and where $m \equiv (ijL_c)$.

At a given probing wavelength $\lambda$, an initial value for x is assigned, based on previously available information (step 701). In step 702, a residual vector y is computed; elements of y are given by the expression in FIG. 1-20. The error function is then evaluated (step 703) in terms of vector y: $F(x)=\frac{1}{2}y^T y$ where $y^T$ is the transpose of y. If this result for $F(x)$ is less than the predefined error threshold (step 704), then the current x is the desired solution for that wavelength. Otherwise, the Jacobian J is computed, and the linearized equation $J\,\Delta x = y$ is solved for $\Delta x$ (step 705). The test solution x is then updated (step 706) to $x+\Delta x$, and the procedure is repeated at step 702 with computation of a new residual vector. Once a solution x below the error threshold is found, the depth-resolved profile at the probing wavelength $\lambda$ is generated (step 707). This procedure is repeated for a set of probing wavelengths (steps 708, 709, 710) to obtain the spectra of the four parameters.

It will be appreciated that the above-described technique may be integrated into endoscopes and used in real time to examine the interior surfaces of an organ without tissue excision. Such a minimally invasive procedure is suited for risk stratification and early detection of cancer. Guided by this technique, suspicious sites may be removed for further evaluation or therapeutic operations can be taken.

The technique is also compatible with other imaging modalities such as fluorescence microscopy. The integration with fluorescence microscopy is potentially rewarding as the combination of morphometry and tumor molecular genetics may provide more accurate diagnoses and more clinically relevant, tumor-specific diagnoses and prognoses.

Data Measurements: Clinical Example

Figure 9B:
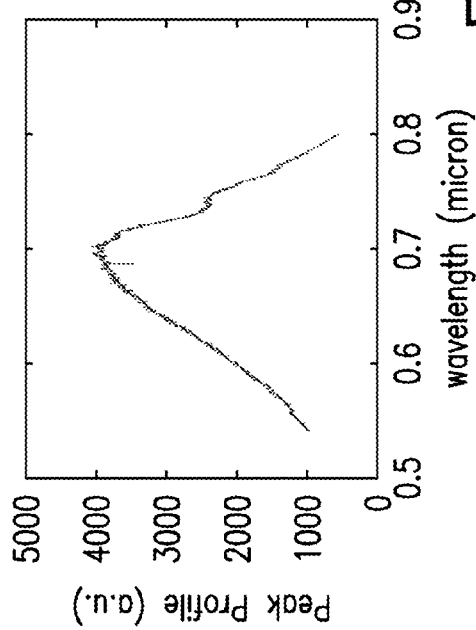
FIGS. 9A-9D show measured data, from a procedure embodying the disclosure, for an adjacent normal tissue site, for comparison with FIGS. 8A-8D respectively.
Figure 9D:
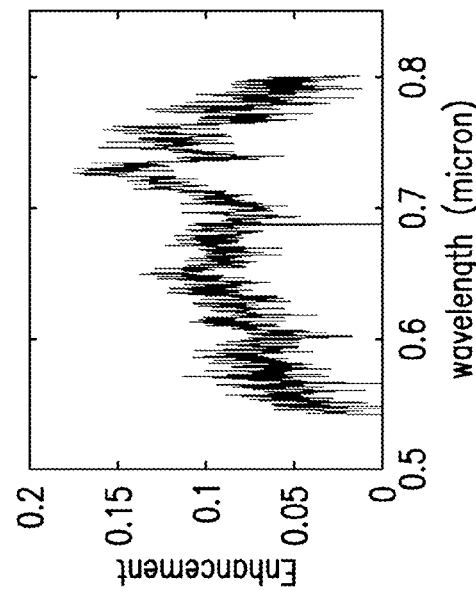
Figure 9A:
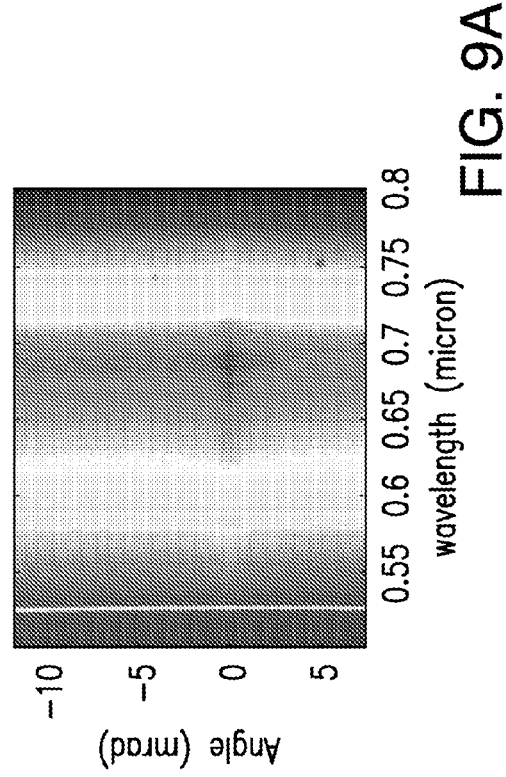
Figure 9C:
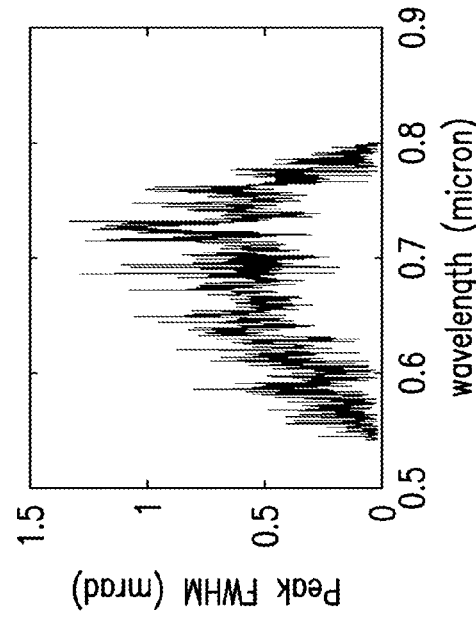

Measured LEBT data for a cancerous tissue site are shown in FIGS. 8A-8D. Corresponding data for an adjacent normal tissue site are shown in FIGS. 9A-9D. FIGS. 8A and 9A are spectral graphs for the enhanced backscattering signal. FIGS. 8B and 9B show the peak profiles. FIGS. 8C and 9C show the full width half maximum (FWHM) of the peaks at various wavelengths. FIGS. 8D and 9D show the enhancement factor as a function of wavelength. Here, enhancement factor may be defined as $E(\lambda)=(I-I')/I'$, where at each wavelength I is the measured intensity of scattered light at zero angle and I' is the measured intensity at an angle displaced from the peak (e.g. −10 mrad, as shown in FIGS. 8A and 9A).

Figure 10:
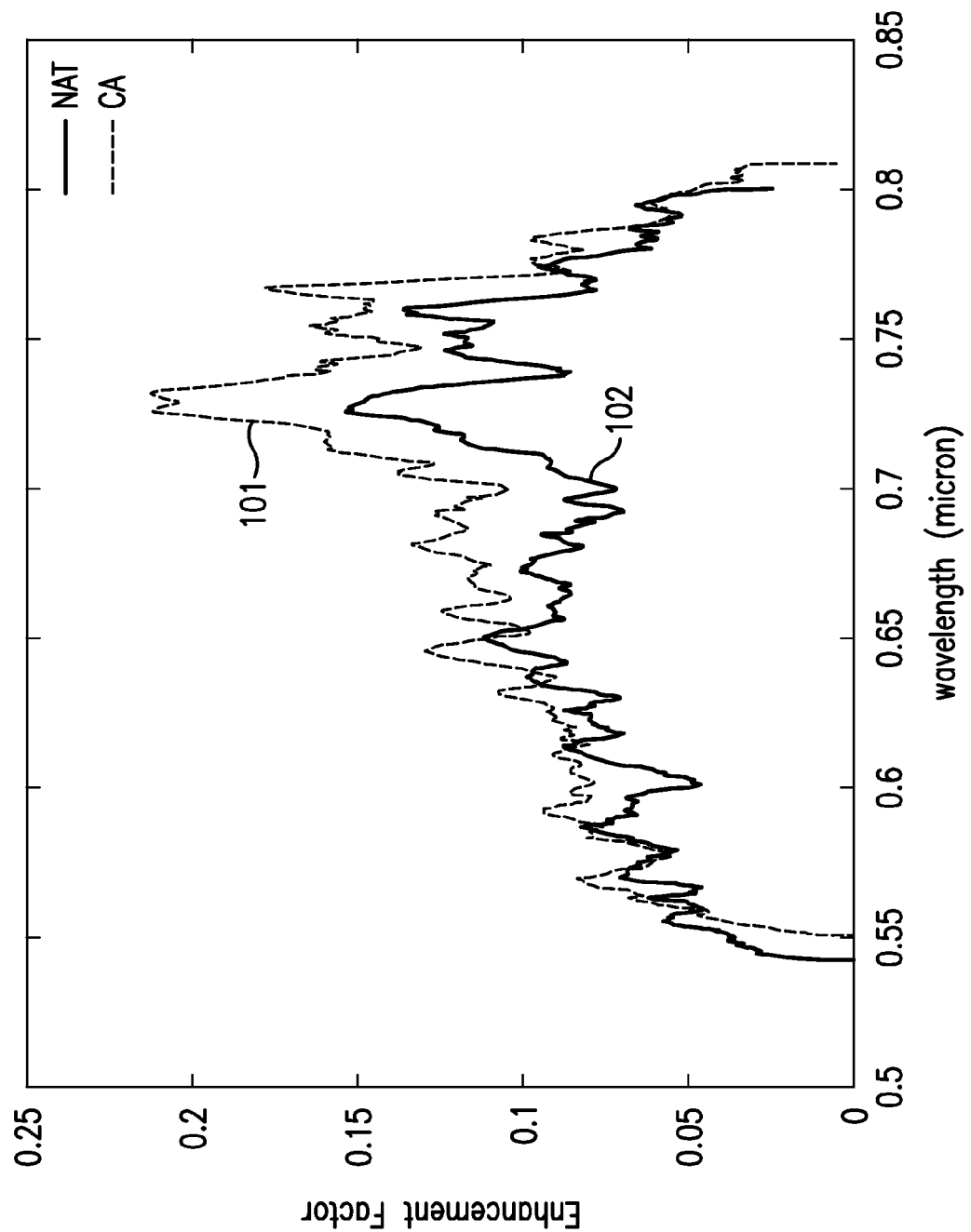

A direct comparison of the enhancement factor results for the cancerous tissue site (graph 101) and the normal tissue site (graph 102), as a function of wavelength, is shown in FIG. 10. A clinical evaluation of a tissue sample may be made in accordance with the enhancement factor results: The cancerous tissue generally shows greater enhancement than the normal tissue, due to stronger light scattering (and thus a shorter transport mean free path) in the cancerous tissue. Over a range of wavelengths (e.g. about 0.55 μm to about 0.72 μm, as shown in FIG. 10), the enhancement factors for cancerous tissue and normal tissue show different trends with increasing wavelength. At the shorter wavelengths (about 0.55 μm) the enhancement factors shown in graphs 101 and 102 are approximately equal, while at longer wavelengths (about 0.72 μm) the enhancement factor for cancerous tissue (graph 101) is greater.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

What is claimed is:

1. A method for noninvasive imaging of tissue, comprising the steps of:
   illuminating a location on a surface of the tissue using an incident beam of light characterized by a spatial coherence length $L_c$;
   detecting light backscattered from the tissue, the backscattered light characterized by a scattering angle θ;
   obtaining spectra from the detected light, each of said spectra characterized by light intensity versus light wavelength λ for a given scattering angle θ at said coherence length $L_c$;
   extracting information regarding both cellular architecture and nuclear morphology of cells in the tissue from the spectra, in accordance with different scattering models for different ranges of scattering angles; and
   constructing a three-dimensional (3D) image of both cellular architecture and nuclear morphology of the cells in the tissue.

2. A method according to claim 1, further comprising:
   recording a two-dimensional (2D) image in accordance with the spectra at the illuminated location;
   scanning the incident beam across the surface to record 2D images corresponding to a plurality of illuminated locations;
   forming a data set of the recorded 2D images; and
   constructing the 3D image from the data set,
   wherein a penetration depth of the light into the tissue corresponds to the spatial coherence length $L_c$, so that the 2D image at a given coherence length $L_c$ is an image for that penetration depth.

3. A method according to claim 1, further comprising:
   recording a two-dimensional (2D) image in accordance with the spectra at the illuminated location;
   wherein said recording step comprises
   computing a model function for the spectra for at least one value of spatial coherence length $L_c$;
   computing an error function in accordance with a difference between the model function and the spectra;
   minimizing the error function, thereby fitting the model function to the spectra;
   constructing the 2D image in accordance with the fitted model functions, for each said value of $L_c$; and
   obtaining a depth profile for the tissue.

4. A method according to claim 3, wherein said scattering includes background cellular scattering and nuclear scattering for cells in the tissue, and the depth profile includes one or more of a nuclear size, a scattering power, a nuclear number density, and a nuclear/cellular scattering ratio.

5. A method according to claim 3, wherein the error function has as arguments one or more of a nuclear size, a scattering power, a nuclear number density, and a nuclear/cellular scattering ratio.

6. A method according to claim 3, wherein the error function has as arguments
   one or more of a nuclear size, a scattering power, a nuclear number density, and a nuclear/cellular scattering ratio; and
   a concentration of one or more absorbing chromophores.

7. A method according to claim 1, wherein in said step of obtaining spectra the coherence length $L_c$ has a plurality of values in a range of about 20 μm to about 200 μm, and for each value of the coherence length $L_c$ the scattering angle θ has a plurality of values from about −5° to about +5° relative to normal to the surface.

8. A method according to claim 1, wherein the tissue is characterized as a plurality of discrete layers, and the backscattered light is characterized as a superposition of light signals from each of the discrete layers.

9. A method according to claim 8, further comprising:
   recording a two-dimensional (2D) image in accordance with the spectra at the illuminated location;
   wherein said recording step comprises
   computing a model function for the spectra at a given spatial coherence length $L_c$;
   constructing an error function in accordance with a difference between the spectra and a model function for the spectra, the error function having as an argument a first vector with elements corresponding to one or more of a nuclear size, a scattering power, a nuclear number density, a nuclear/cellular scattering ratio, a concentration of deoxy-hemoglobin, and a concentration of oxy-hemoglobin for each of the layers;
   computing a second vector, characterized as a residual vector, with elements corresponding to a difference between the model function and the spectra at the given coherence length for a given light wavelength and a given scattering angle;
   computing a value for the error function in terms of the residual vector;
   determining whether said value for the error function is less than a predefined error threshold value, and if said value for the error function is less than the error threshold value, fitting the model function to the spectra; and
   constructing
   a depth profile for the tissue.

10. A method according to claim 1, wherein information regarding the nuclear morphology of the cells is obtained from the spectra in accordance with a nuclear Mie scattering model; and
   information regarding the cellular architecture is obtained from the spectra in accordance with a background fractal scattering model.

11. A method according to claim 1, wherein the incident beam of light is partially spatially coherent light or coherent light.

12. A method according to claim 1, wherein
   the incident beam of light is partially spatially coherent or coherent light, and
   each of said spectra is obtained from a measurement of light intensity for at least one wavelength λ, at least one scattering angle θ, and at least one coherence length $L_c$.

13. A method for noninvasive imaging of tissue, comprising the steps of:
   illuminating a location on a surface of the tissue using an incident beam of light characterized by a wavelength λ and a spatial coherence length $L_c$;
   detecting light backscattered from the tissue, the backscattered light characterized by a scattering angle θ;

calculating a signal intensity at each of a set of wavelengths $\lambda$ in terms of quantities $\mu_s$, $p_b$, $<\theta^2>$, and $\mu_a$, thereby obtaining spectra, said quantities determined by cellular architecture and nuclear morphology of cells in the tissue, where $\mu_s$ is a scattering coefficient of the tissue, $p_b$ is given by a ratio of the strength of light scattering into angles larger than about 5° to the strength of light scattering into angles smaller than about 5°, $<\theta^2>$ is the mean squared scattering angle, and $\mu_a$ is an absorption coefficient of the tissue;

extracting information regarding both cellular architecture and nuclear morphology of cells in the tissue from the spectra, in accordance with different scattering models for different ranges of scattering angles; and obtaining a depth-resolved profile for the tissue.

14. A method according to claim 13, wherein said calculating step includes minimizing an error function.

15. A method according to claim 13, wherein the tissue is characterized as a plurality of discrete layers, and the backscattered light is characterized as a superposition of light signals from each of the discrete layers.

16. A method according to claim 13, wherein the light is scattered from a maximum depth of about 100 μm below the surface.

17. A method according to claim 13, wherein said calculating step includes calculating a first signal intensity, characterized as I, at a given wavelength $\lambda$ for $\theta=0$;

calculating a second signal intensity, characterized as I', at said wavelength $\lambda$ for a selected angle $\theta \neq 0$; and determining an enhancement factor $E(\lambda)=(I-I')/I'$.

18. A method according to claim 17, further comprising performing a clinical evaluation of said tissue sample in accordance with the enhancement factor.

19. A method according to claim 13, wherein the incident beam of light is partially spatially coherent light or coherent light.

20. A method according to claim 13, wherein the spectra are obtained for a fixed spatial coherence length $L_c$.

* * * * *